United States Patent [19]

Lieber et al.

[11] Patent Number: 5,029,585
[45] Date of Patent: Jul. 9, 1991

[54] COMFORMABLE INTRALUMEN ELECTRODES

[75] Inventors: Clement E. Lieber, Yorba Linda; Edward E. Elson, Anaheim, both of Calif.

[73] Assignee: Baxter International Inc., Deerfield, Ill.

[21] Appl. No.: 380,052

[22] Filed: Jul. 14, 1989

[51] Int. Cl.$^5$ .................... A61B 5/0402; A61N 1/05
[52] U.S. Cl. .................... 128/642; 128/786; 29/854; 29/14
[58] Field of Search ........ 128/642, 692, 693, 784–786, 128/419 P; 29/854

[56] References Cited

U.S. PATENT DOCUMENTS

| 4,073,287 | 2/1978 | Bradley et al. | 128/642 |
| 4,198,991 | 4/1980 | Harris | 128/784 |
| 4,595,012 | 6/1986 | Weber et al. | 128/642 |

FOREIGN PATENT DOCUMENTS 0101595  2/1984  European Pat. Off. ............ 128/642

Primary Examiner—Lee S. Cohen
Attorney, Agent, or Firm—Debra D. Condino

[57] ABSTRACT

The present invention provides conformable intralumen electrodes for use with medical catheters. The electrodes are made of a conductive polymeric material that is introduced into the lumen of a catheter through an opening cut in the peripheral wall in the catheter. A conductive lead threaded through the lumen of the catheter terminates in a distal end at the opening in the catheter and is completely embedded within the polymeric material introduced into the opening, thereby establishing electrical contact between the conductive polymeric electrode and the conductive lead. The conductive polymeric material fills the opening adhering to the walls of the catheter tube, thereby ensuring secure, long lasting attachment.

14 Claims, 3 Drawing Sheets

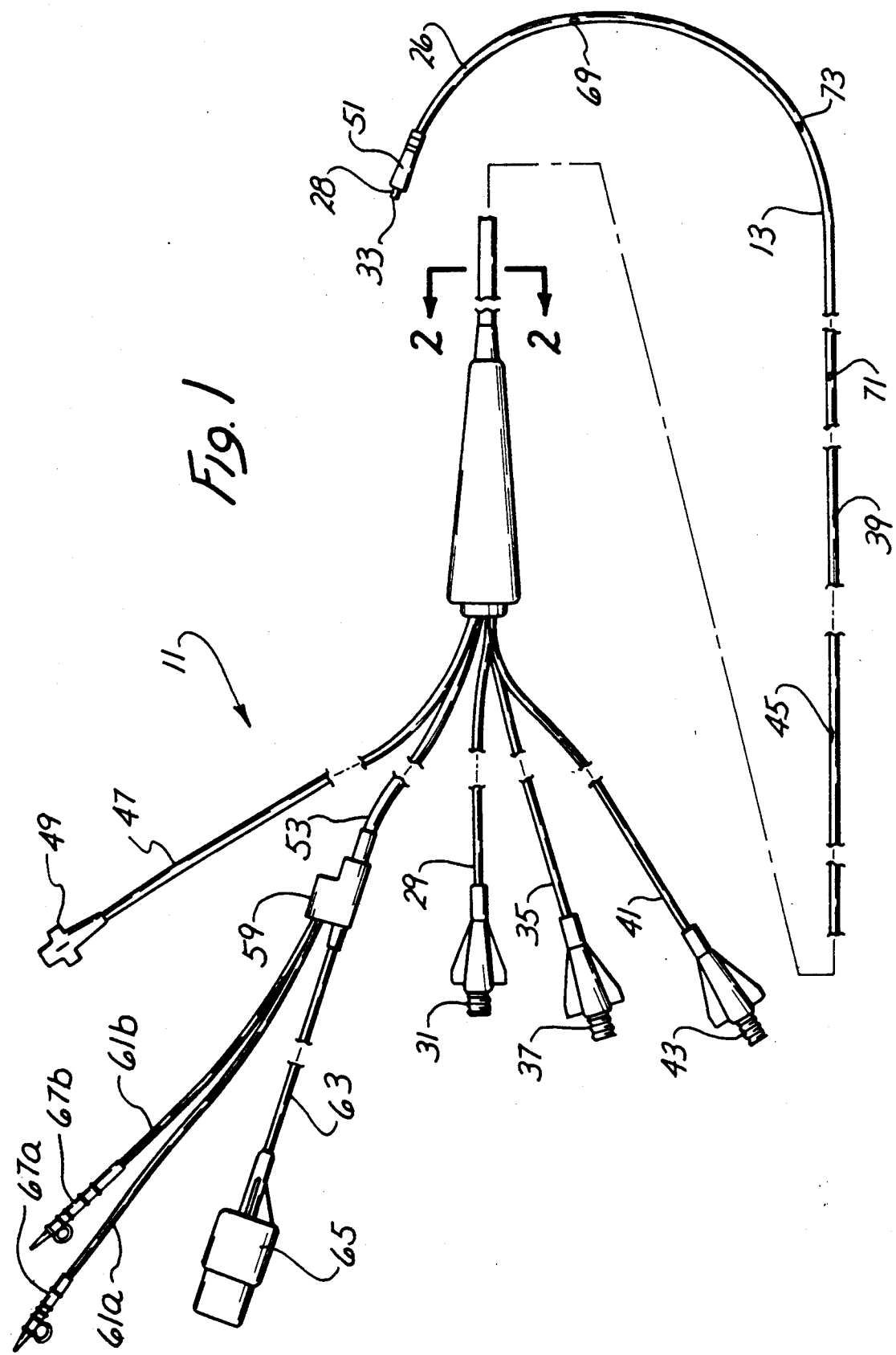

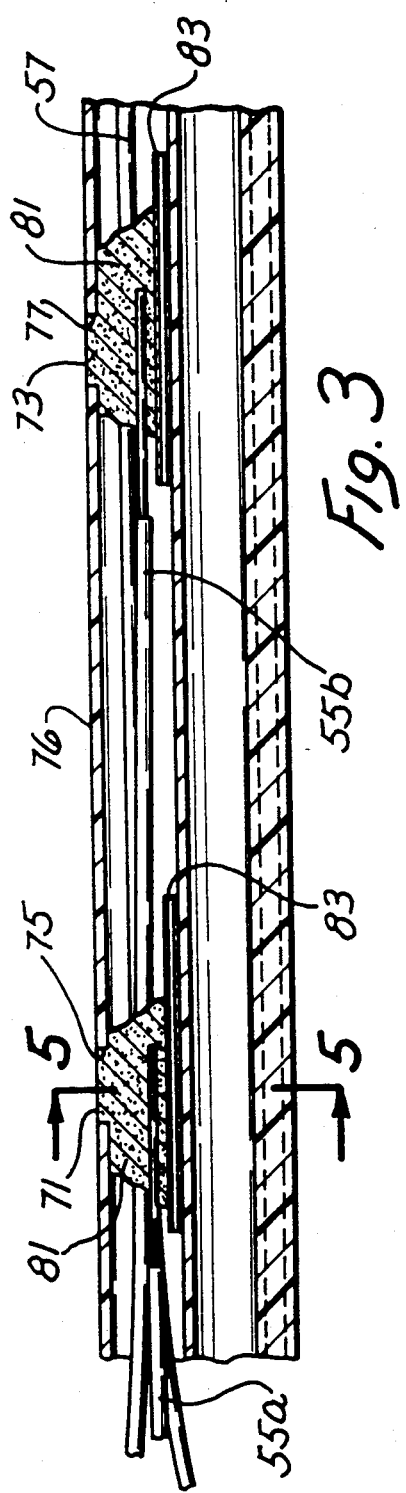
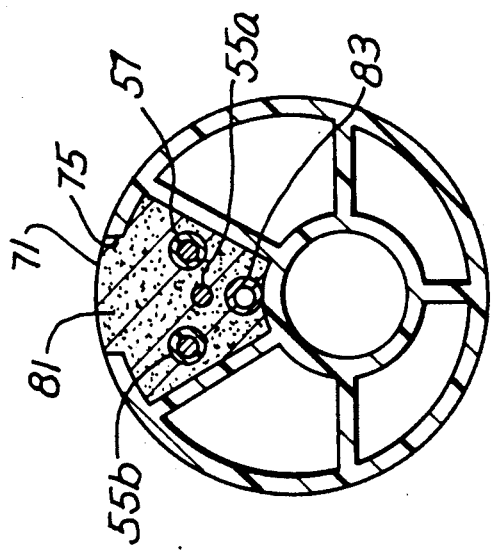
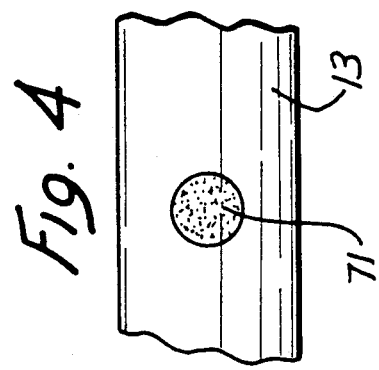
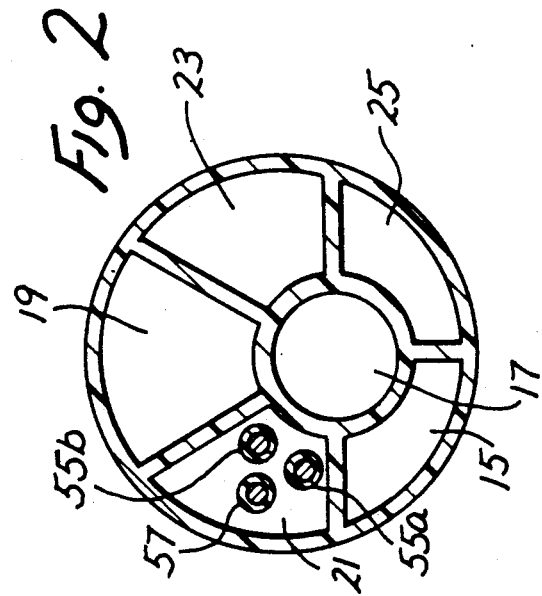

COMFORMABLE INTRALUMEN ELECTRODES

FIELD OF INVENTION

The present invention relates to electrodes mounted within a lumen of a catheter for medical use and a method of mounting electrodes in the catheter lumen.

BACKGROUND OF THE INVENTION

Various medical procedures require the making of electrical contact with specified regions within the heart. For example, in an intracardiac ECG (electrocardiogram), an apparatus such as a catheter or a probe is inserted through a vein or an artery into the appropriate location within the heart. The apparatus has one or more electrodes which are placed in close proximity to the tissue of the heart so that the electrical activity within the heart can be appropriately monitored. Intracardiac ECG sensing can be done when the apparatus is in the heart for other purposes, such as pressure monitoring, measuring cardiac output or right heart ejection fraction.

Similarly, impedance measurements to determine physiological functions or parameters, such as for example, blood flow, chamber volumes and continuous cardiac output, require electrical contact between two or more electrodes and the body. For impedance measurements, electrodes are typically mounted on a catheter and inserted into the vascular system or the heart, or into other parts of the body depending upon where the impedance measurements are to be taken.

Temporary pacing of the heart also requires the making of electrical contact between one or more electrodes of an apparatus, such as a probe or catheter, and the tissue of the heart. For example, during certain surgeries a catheter may be inserted into the heart to monitor various cardiovascular functions, such as cardiac output or right heart ejection fraction. Such a catheter may be equipped with appropriate pacing electrodes so that, if the patient should suffer a cardiac arrest, the heart can be quickly given the necessary electrical therapy.

It is conventional practice to mount the electrodes on the exterior surface of a catheter, and constructions of this type are shown, for example, in Blake et al., U.S. Pat. No. 3,995,623 for a Multipurpose Flow-Directed Catheter, issued Dec. 7, 1976. Unfortunately, there is a danger that electrodes mounted on the exterior of the catheter may become loose and slide off the catheter and remain in the patient. This can occur, for example, as a result of sliding the catheter through a tubular introducer which is used in placement of the catheter. In addition, an electrode mounted on the exterior of the catheter tends to project radially beyond the catheter body line and, as such, is more likely to slide off the catheter as a result of relative movement between the catheter and the introducer.

U.S. Pat. No. 4,595,012, issued June 17, 1986, for Lumen Mounted Electrodes for Pacing and Intra-Cardiac ECG Sensing, in the name of Webler, et al., which is incorporated herein by reference in its entirety, sought to solve this problem by mounting a tubular metal electrode within a lumen of a catheter and by placing the mounting means for the electrode at least partially within the lumen. To make the dismounting of the electrode even less likely and to reduce the likelihood of the electrodes forming an impediment to movement of the apparatus, the electrode and the mounting means lie radially inwardly of the body line of the apparatus.

In Webler, the electrodes are tubular conductive members or sleeves of a suitable conductive biocompatible metal such as stainless steel. The mounting means includes a tubular, resiliently bendable mounting member of a suitable nontoxic material, such as polyvinylchloride. The cylindrical mounting member forms a sliding fit within the cylindrical axial passage of the tubular electrode. The mounting member extends completely through the electrode and has end portions in the lumen on opposite sides of the electrode that form a mechanical interlock with the catheter tube on opposite sides of the port opening. The mounting means also includes an insulating adhesive, such as urethane, which bonds the electrode to the mounting member and bonds both of these members within the lumen and to the catheter tube.

The use of a conductive polymer on the tip of a body implantable lead for pacing is known. See for example European Patent Application No. 0057450, published Nov. 8, 1982. The cardiac pacing lead disclosed in the European application comprises a coiled flexible conductor and an overlying sheath. The conductor is in electrical communication with a polymer gel electrode by means of a metal crimp-sleeve. The sheath provides electrical insulation for the conductor. The lead body defines a cavity at the distal end which contains the polymer electrode with a rounded end portion extending beyond the open distal end of the lead body. The rounded end provides electrical contact between living tissue and the conductor. The polymer electrode consists of a conductive polymer gel, preferably a hydrogel which extends out of the lead body for about 0.5 mm to about 1.0 mm.

The European application also discloses a second embodiment wherein a ring-electrode for a bipolar lead is provided and includes a second flexible conductor and a band of the polymer gel formed over the insulating sheath but in contact with the second conductor.

U.S. Pat. No. 4,198,991, entitled Cardiac Pacer Lead issued Apr. 22, 1980 in the name of Harris, discloses a cardiac pacer lead utilizing as a conductive element a thread of conductive carbon filaments in a resin matrix. The thread is helically wound between a stimulation electrode structure at the distal end of the lead and a terminal at the proximal end. To establish the electrical connection at each end of the conductive element, the carbon filaments are first bared and then bonded with a conductive, e.g., silver or platinum-loaded, epoxy adhesive to the metal electrode and terminal components. See Column 3, line 31–40.

U.S. Pat. No. 3,721,246, entitled Applicator Electrode with a Very Thin Non-Metallic Current Distributing Layer, issued Mar. 20, 1973 in the name of Landis, discloses a body contacting electrode. The electrode has a dry, current distributing, skin contacting layer selectively disposed adjacent a conductive portion to provide a high resistance electrode arranged to limit and uniformly disperse the current from an electrical source through the skin area adjacent the electrodes. The current distributing layer is comprised preferably of conductive particles such as carbon or the like, uniformly distributed in a nonconducting plastic medium such as epoxy or other insulating material. Means are provided to couple the electrode to an external electrical source and to releasably support the electrode adjacent a preselected area of the body.

SUMMARY AND OBJECTS OF THE INVENTION

An object of the present invention is to provide a catheter for medical use with one or more electrodes disposed within the lumen of the catheter such that the electrode conforms to the size and shape of the lumen. It is another object of the present invention to provide a catheter with electrodes disposed within a lumen such that they adhere to the walls of the catheter tube to prevent loss or removal within a patient.

A further object of the present invention is to provide a catheter with electrodes that can be securely mated to a transmitting wire without the use of thermal energy or welding to assure a connection.

It is another object of the present invention to provide a low cost alternative to ring or bar electrodes conventionally used on catheters or in catheter lumens for the purpose of providing an electrical stimulus or receiving an electrical signal from the heart.

It is another object of the present invention to provide an electrode that can be easily placed within a lumen of the catheter without mechanical mounting means and without deforming the parent body material of the catheter.

It is another object of the present invention to provide a catheter with electrodes that conform to the surface of the catheter to minimize problems such as tissue abrasion and blood clot formation.

In general, the present invention provides conformable intralumen electrodes for mounting in catheters for medical use. The electrodes are made of a conductive polymeric material comprising a nonconductive or insulating polymeric base material with conductive material uniformly dispersed therein. The base material may comprise a polymeric resin, preferably with adhesive properties, such as an epoxy resin, or may comprise a polymeric thermoplastic material, such as polyvinyl-chloride. The conductive material dispersed within the base material may be any conductive metal particles such as silver, gold, platinum, carbon or the like.

The catheter is preferably an elongated tube, preferably formed of an extruded biocompatible material, such as polyvinylchloride, and is sized to pass through a vein or an artery into the heart or into another desired area or organ of the body.

The catheter has proximal and distal ends, a peripheral wall and at least one lumen, typically two or more extending longitudinally within the tube. An opening in the peripheral wall of the catheter communicates with the lumen. At least one conductive lead is disposed within the lumen from the opening to the proximal end of the catheter. The conductive polymeric material is introduced into the lumen at the opening and fills the opening adhering to the walls of the catheter tube. The distal end of the conductive lead is thus completely embedded within the conductive polymeric material ensuring electrical continuity and secure, long lasting attachment.

The conductive polymeric material is introduced into the opening of the lumen in a semiliquid form and may be extruded or pressed into the opening without deforming the parent body material. If the conductive polymeric material has a thermoplastic base, it may be injection molded into the opening. Upon curing, the conductive polymeric material will be held in place in the lumen by adhesion to the parent material. Preferably, the polymeric material extends proximally and distally some distance beyond the entrance port location which thereby increases the surface area for adhesion and insures that the electrode will be locked or permanently retained within the lumen. The surface area of the electrode can be altered by increasing or decreasing the surface opening of the port through which the polymeric material is introduced so that the appropriate current density is achieved.

It is also preferred that the electrode not extend beyond the outer peripheral surface of the catheter. By use of appropriate solvents or mechanical means, the conductive polymeric material can be shaped to conform to the outer surface.

Additionally, it is preferred that venting means be provided through the conductive polymeric material to create an air path through the lumen. The air path enables the entire lumen to be sterilized during gas sterilization and also creates a pathway for other purposes if needed. For example, the lumen containing the electrodes could also be used as the inflation lumen for a balloon at the distal tip of the catheter thus, eliminating the need for an additional inflation lumen.

The venting means is preferably tubular and resiliently bendable so that it can be introduced into the lumen through the port opening prior to introducing the conductive polymeric material into the opening.

The electrodes of the present invention are ideally suited for mounting in a flow directed balloon catheter that includes at least two lumens, one lumen for the electrode or electrodes, preferably two electrodes are provided, which is also used for balloon inflation through the vent tubes as described above, and a second lumen for monitoring pressure at the distal tip and measuring wedge pressure when the balloon is inflated. Most often, a third lumen would be provided for balloon inflation.

The electrodes are also ideally suited for thermodilution catheters which include an additional lumen for injecting fluid for thermodilution measurements or for infusing medication as needed, and a thermistor proximal to the distal tip for measuring the temperature of the bloodstream.

When the catheter is in place in a patient, the electrodes are immediately available as needed for ECG monitoring and impedance measurements. While the electrodes can also be used for intracardiac pacing, they are more particularly suited for ECG sensing and impedance measurements. For ECG monitoring, the electrodes are positioned within the lumen so that when the catheter is in the wedge position, one electrode is in the right ventricle and one electrode is in the pulmonary artery. For impedance measurements to determine blood flow, chamber volume or continuous cardiac output, two or more, usually three to six electrodes are positioned along the length of the catheter usually that portion of the catheter positioned in the right ventricle.

For pacing, the electrodes are preferably positioned relative to the distal tip of the catheter so that when the distal tip is in the pulmonary artery wedge position, one electrode is in the right atrium and one electrode is in the right ventricle. Stiffeners should be provided in the catheter to ensure that the catheter bends within the heart to place the electrodes in close proximity or in contact with the walls of the heart as disclosed in U.S. Pat. No. 3,995,623 to Blake et al. which is incorporated herein by reference in its entirety.

The electrodes of the present invention are particularly useful in an intravascular diagnostic catheter that measures right heart ejection fraction. A right heart election fraction and cardiac output catheter is disclosed in commonly assigned U.S. Pat. No. 4,632,125, issued Dec. 30, 1986, in the name of Webler, et al. which is hereby incorporated by reference in its entirety. The method of calculating right heart ejection fraction using thermal dilution techniques and ECG monitoring is disclosed in commonly assigned, co-pending U.S. patent application Ser. No. 866,772, filed May 23, 1986, now U.S. Pat. No. 4,858,618, in the name of Konno, et al., which is hereby incorporated by reference in its entirety.

BRIEF DESCRIPTION OF THE DRAWINGS

FIG. 1 is a plan view of a right heart ejection fraction and cardiac output catheter containing the electrodes of the present invention.

FIG. 2 is a cross-sectional view of the catheter taken along line 2—2 of FIG. 1.

FIG. 3 is a longitudinal, fragmentary sectional view through the portions of the catheter which include the electrodes of the present invention.

FIG. 4 is a top, plan fragmentary view of a portion of the catheter at the site of an electrode constructed in accordance with the present invention.

FIG. 5 is a cross-sectional view of the catheter taken along line 5—5 of FIG. 3.

DETAILED DESCRIPTION OF THE PREFERRED EMBODIMENT

Figure 6:
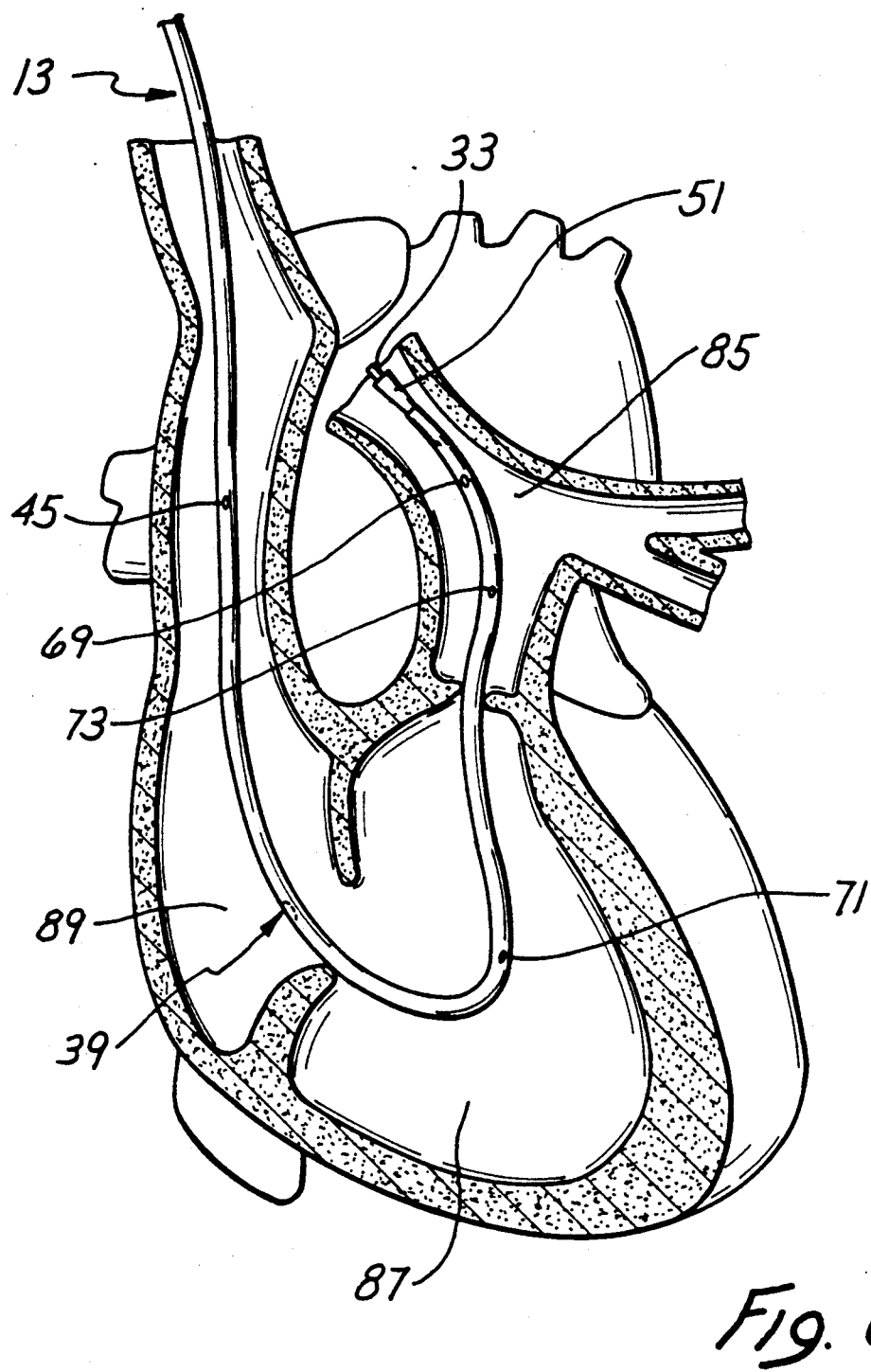
FIG. 6 is a sectional view of the human heart with the catheter in position.

FIG. 1 shows a right heart ejection fraction and cardiac output catheter 11 that includes the conformable intralumen electrodes of the present invention. Catheter 11 comprises an elongated catheter tube 13 extruded from a suitable biocompatible plastic material, preferably polyvinylchloride. The catheter tube 13 is flexible, elongated and sized to be received within a vein or artery and passed into the heart. The catheter tube 13 shown in FIG. 1 has six lumens (see FIG. 2), a balloon inflation lumen 15, a through lumen 17, an injectate lumen 19, an electrode/thermistor lead lumen 21, an infusion lumen 23, and an extra lumen 25 for any other diagnostic or monitoring purpose desired. By way of example the extra lumen may be used as an oximeter for fiber optic measurements of oxygen saturation in the blood.

The catheter 13 has a curved distal end portion 26. The curve in the distal end portion is preformed so that the distal end portion assumes the curved configuration when it is under no external force. Although the curve may be of varying lengths and radii, in the embodiment illustrated, the curve extends for approximately 170 degrees, beginning at a location about 10 cm. from the distal tip 28 and terminating at the distal tip 28. This feature of the catheter embodiment shown in FIG. 1 is more fully described in U.S. Pat. No. 4,632,125 which was previously incorporated herein by reference.

The through lumen 17 extends continuously from the proximal end of the catheter tube 13 at connector 27 to the distal end 28 and terminates at the distal end 28 where it opens at a distal port 33. Extension tube 29 is connected to the through lumen 17 at connector 27 and has proximal connector 31 for attachment to pressure monitoring apparatus so that wedge pressures and pulmonary artery pressures can be measured at distal port 33.

The injectate lumen 19 extends continuously from the proximal end of the catheter tube 13 to a location proximal to the curved distal end portion 26. An injectate port 39 cut through the peripheral wall of the catheter tube 13 provides communication between the injectate lumen 19 and the exterior of the tube. Preferably, the injectate port 39 comprises a plurality of openings and in the embodiment illustrated in FIG. 1, three of such openings are provided. A greater volume of injectate can then be delivered to the bloodstream through port 39, in a shorter period of time than if one opening were used. The construction and positioning of the injectate port is more fully described in U.S. Pat. No. 4,632,125 which was previously incorporated herein by reference.

Extension tube 35 is connected to the injectate lumen 19 at connector 27 and has proximal connector 37 for attachment to an injectate source. The injectate port is typically located about 16 to 30 cm from the distal tip of the catheter, so that when the catheter is properly positioned within the heart of most adult patients, the injectate port is in the right atrium closely adjacent the tricuspid valve and in close proximity to the inferior vena cava. Lumen 19 is closed distally of the injectate port by a plug inserted through port 39 and adhesive applied around the plug.

Infusion lumen 23 extends continuously from the proximal end of the catheter tube 13 to a location proximal to the injectate port. An infusion port 45 extends through the peripheral wall of the catheter tube to provide communication between the infusion lumen 23 and the exterior of the tube. Lumen 23 is closed distally of port 45 by a plug inserted through port 45 and adhesive applied around the plug. Extension tube 41 is connected to infusion lumen 23 at connector 27 and has proximal connector 43 for attachment to an infusion source. Medication or other fluids may then be infused to the patient through infusion port 45 which is typically located about 30 to 45 cm from the distal tip of catheter so that when the catheter is in place in the heart, the infusion port opens into the superior or inferior vena cava.

The inflation lumen extends continuously from the proximal end of the catheter tube 13 to the balloon 51 positioned closely adjacent to the distal tip 28. An inflation port (not shown) cut in the peripheral wall of the catheter tube to provides communication between the inflation lumen and the interior of the balloon 51. Extension tube 47 is connected to the inflation lumen 15 and has proximal connector 49 for attachment to an air source for inflating the balloon 51.

Extension tube 53 is attached to the electrode/thermistor lumen 21 at connector 27. Electrode leads 55a and 55b and thermistor leads 57 are threaded proximally through lumen 21 and extension tube 53, and are separated at connector 59 into separate conduits 61a and 61b for the electrode leads and conduit 63 for the thermistor lead. Thermistor coupler 65 and electrode couplers 67a and 67b may then be coupled to appropriate electronic monitoring equipment.

Since lumen 25 is not in use in the catheter embodiment shown, there is no extension tube connected to the lumen. If the lumen were being used for measuring oxygen saturation or for some other monitoring function, an additional extension tube and port opening would be provided.

The catheter 11 includes a temperature sensor in the form of a thermistor 69 located just proximal to the balloon at approximately 4–6 cm. In the catheter embodiment shown in FIG. 1, the thermistor is a fast response thermistor which is needed to accurately measure right heart ejection fraction. While various temperature sensors and temperature sensor mounting constructions may be employed, it is preferred to use a thermistor in the form of a thermistor bead mounted as described in commonly assigned U.S. Pat. No. 4,796,640, issued Jan. 10, 1989, in the name of Webler, for an Apparatus with Fast Response Thermistor, the disclosure of which is incorporated herein by reference in its entirety.

The catheter 11 also includes two conformable intralumen electrodes of the present invention, a proximal electrode 71 and a distal electrode 73. In the catheter embodiment shown in FIG. 1, electrode leads 55a and 55b and thermistor lead 57 are threaded distally through lumen 21 until a location just distal of the plug in the injectate lumen at which point the electrode and thermistor leads are crossed over from lumen 21 into injectate lumen 19. This crossover technique is known and described in U.S. Pat. No. 4,632,125 previously incorporated herein by reference. Briefly, an opening is cut in the partition between the injectate lumen 19 and the electrode/thermistor lead lumen 23 by inserting a blade through the previously cut injectate port. The leads are then threaded through lumen 21 and through the crossover opening into lumen 19. The crossover opening is then sealed with adhesive.

There are many possible constructions for a catheter utilizing the conformable intralumen electrodes of the present invention. For example, the electrode leads and electrodes may be contained in a single lumen without a crossover or a crossover may be from the electrode lead lumen into the infusion lumen as opposed to the injectate lumen, depending upon the desired placement of the electrodes relative to the distal tip of the catheter. The electrode leads and thermistor leads may also extend distally to the location of the thermistor at which point they are crossed over into the distal portion of the injectate or infusion lumen and the electrode leads are threaded proximally to the location of the two electrodes, respectively.

In the six lumen catheter embodiment shown in FIG. 1, the lumens are narrower in diameter than in a three or four lumen catheter. The largest lumen 19 is therefore needed to quickly deliver the volume of injectate required for right heart ejection fraction (RHEF) determinations. The largest lumen also provides the space needed for the conformable intralumen electrodes and for potting the thermistor bead. Thus, a crossover into the distal portion of the injectate lumen is preferable in a six lumen catheter embodiment.

In the catheter embodiment shown in FIG. 1, electrode lead 55a therefore crosses from lumen 21 to lumen 19 at the crossover point (not shown) and terminates at a proximal opening 75 in the peripheral wall 76 of the catheter tube 13. Electrode lead 55b crosses over from lumen 21 to lumen 19 at the crossover point extends past the proximal opening 75 and terminates at a distal opening 77 in the catheter tube. Thermistor lead 57 crosses over from lumen 21 to lumen 19 at the crossover point, extends past the proximal and distal openings 77 and 79 and terminates at thermistor 69.

The electrodes 71 and 73 are made of a conductive polymeric material 81, preferably a nonconductive or insulating polymeric base material with conductive material uniformly dispersed therein. Preferred polymeric base materials are polymeric resins with adhesive properties, such as epoxy. Thermoplastic polymeric materials that can be injection molded into the lumen of the catheter and that bond with the parent material upon curing, such as polyvinylchloride, can also be used. Suitable conductive particles for dispersing in the base material include silver, platinum, carbon or the like. A conductive silver epoxy adhesive is particularly suitable for forming the electrodes of the present invention and is commercially available from Tra-Con Inc. under the trademark Tra-Duct 2902.

The conductive polymeric material 81 is introduced into lumen 19 at openings 75 and 77, coating the distal ends of electrode leads 55a and 55b so that the distal ends are completely embedded within the conductive polymeric material. This assures good electrical contact and secure, long lasting attachment. The electrode leads, typically nickel alloy wires, are encased in an insulating sheath except at the distal ends which are exposed to make electrical contact with the conductive polymeric material 81.

The conductive polymeric material 81 is introduced into the opening of the lumen in a semiliquid form and may be extruded or pressed into the opening without deforming the parent body material. The electrode may be formed in position under or beneath the edges of the cavity to permanently maintain it in position. Upon curing, the conductive polymeric material will be held in place in the lumen by adhesion to the walls of the catheter tube 13. Preferably, the polymeric material extends proximally and distally some distance beyond the entrance port location which thereby increases the surface area for adhesion and insures that the electrode will be locked or permanently retained within the lumen. The conductive polymeric also seals the port opening, thereby preventing leakage of blood or other body fluids into the catheter at the site of the electrodes.

The surface area of the electrode can be altered by increasing or decreasing the size of the port opening in the peripheral wall of the catheter through which the polymeric material is introduced so that the appropriate current density is achieved. It is also preferred that the electrode not extend beyond the outer peripheral surface of peripheral wall 76 of the catheter. By use of appropriate solvents or mechanical means, the conductive polymeric material can be shaped to conform to the outer surface to minimize problems such as tissue abrasion and blood clot formation.

Additionally, it is preferred that venting means 83 be provided through the conductive polymeric material to create an air path through the lumen. The air path enables the entire lumen to be sterilized during gas sterilization and also creates a pathway for other purposes if needed. For example, one lumen could be used for balloon inflation and the electrodes.

The venting means 83 is preferably tubular and resiliently bendable so that it can be introduced into the lumen through the port openings prior to introducing the conductive polymeric material into the opening. The venting means is preferably made of polyvinylchloride but other biocompatible polymeric materials may be used.

The intralumen electrodes and electrode forming process of the present invention eliminate the need for costly ring or bar electrodes which are generally welded to conductive wires for the purpose of providing an electrical signal from the heart. The process of the present invention provides a method of securely mating an electrode to a transmitting wire without the use of thermal energy or welding to assure electrical connection. The process also eliminates complicated mechanical mechanisms for retaining bar or cylinder electrodes in the lumen of a catheter.

The process also allows for an electrode to conform to the size and shape of the cavity opening or lumen so that no pre-formed electrodes are required. The electrode forming process of the present invention also eliminates the need for preformed ring electrodes around the exterior of the catheter which may be forced off over the catheter body and become trapped within the heart.

The intralumen electrodes of the present invention are particularly suited for intracardiac ECG monitoring and for taking impedance measurements to determine phsyiological parameters such as blood flow, heart chamber volumes, and continuous cardiac output. The electrodes of the present invention may also be used to take impedance measurements at other locations within the body and may be used for intracardiac pacing.

For pacing, the electrodes are preferably positioned at proximal and distal positions along the length of the catheter so that when the catheter is in place in the patient's heart, one electrode is in the right atrium (23-25 cm from the distal tip) and one electrode is in the right ventricle (about 15-16 cm form the distal tip). For pacing, stiffeners should be provided in the catheter to insure that the catheter bends within the heart to place the electrodes in close proximity or in contact with the walls of the heart. A stiffener for this purpose is described in Blake et al. U.S. Pat. No. 3,995,623 previously incorporated herein by reference.

Electrodes positioned for pacing can also be used for ECG monitoring, but preferably for ECG monitoring the electrodes are positioned within the lumen so that when the catheter is in place within the patient's heart, the proximal electrode is in the right ventricle, preferably close to the apex of the right ventricle and the distal electrode is in the pulmonary artery, preferably at a point just distal of the pulmonic valve. Proximal and distal electrodes 71 and 73 in catheter tube 13 are so positioned. Typically, in most adult patients this positioning can be accomplished by locating the distal electrode 73 within the catheter at about 6 to 8 cm from the distal tip and the proximal electrode at about 14 to 18 cm from the distal tip.

The electrodes positioned for ECG sensing are also suitable for impedance measurements within the heart. For impedance measurements, however, it is often desirable to include more than two electrodes, usually three to six, along the length of the catheter portion which is typically positioned in the right ventricle. For example, in the catheter embodiment shown in FIG. 1, they would be positioned from a point just distal to the injectate port 39 to a point just proximal to the thermistor 69.

FIG. 4 shows a top plan view of the intralumen electrode of the present invention and FIG. 5 shows a cross-sectional view of proximal electrode 71 taken along line 5—5 of FIG. 3.

In use of the catheter 11, the catheter tube 13 is introduced through a vein or an artery of a patient and into the heart (FIG. 7) using known techniques. The balloon 51 is inflated through the balloon inflation lumen 15 and the inflated balloon is used to carry the distal end 28 of the catheter 11 to the desired location. FIG. 6 shows catheter 11 positioned within the heart with the balloon 51 in the pulmonary artery 85.

The location of the catheter tube 13 within the heart will, of course, depend upon the procedure being carried out. For example, for intra-cardial ECG, the catheter tube 13 is inserted into the heart to place the electrodes 71 and 73 in the right ventricle 87 and pulmonary artery 85, respectively. Electrodes 71 and 73 are in proximity to the heart tissue across the appropriate portion of the heart's electrical field so that they can sense the electrical activity within the heart in a known manner. For pacing, the electrodes 71 and 73 should be positioned in the right atrium 89 and the right ventricle 87, respectively. The catheter tube 13 may be placed within the heart solely for intra-cardial ECG sensing or temporary pacing or for other purposes, such as monitoring of the cardiovascular system.

Although an exemplary embodiment of the invention has been shown and described, many changes, modifications and substitutions may be made by one having ordinary skill in the art without necessarily departing from the spirit and scope of this invention.

What is claimed is:

1. An apparatus for making electrical contact within the body of a patient comprising:
   (a) an elongated tube sized to be received within a selected portion of the body, having proximal and distal ends, a peripheral wall having an outer peripheral surface, at least one lumen extending longitudinally within the tube and an opening in the peripheral wall which extends from the lumen to the exterior of the tube, said opening sized to expose a selected surface area of an electrode to be formed therein;
   (b) the electrode comprising a conductive polymeric material filling said opening and extending into said lumen proximally and distally of said opening and extending radially outwardly no farther than the outer peripheral surface;
   (c) at least one conductive lead having a distal end embedded within the conductive polymeric material and extending from said electrode within the tube to the proximal end of the tube; and
   (d) a passageway extending longitudinally through the conductive polymeric material within said lumen.

2. An apparatus according to claim 1, wherein said conductive polymeric material comprises a nonconductive or insulating polymeric base material with conductive particles uniformly dispersed therein.

3. An apparatus according to claim 2, wherein said conductive particles are selected from the group consisting of silver, gold, platinum and carbon.

4. An apparatus according to claim 1, wherein the conductive polymeric material is a resin with adhesive properties and has conductive particles uniformly dispersed therein.

5. An apparatus according to claim 4, wherein the conductive polymeric material is a conductive epoxy adhesive.

6. An apparatus according to claim 5, wherein the conductive epoxy adhesive has silver particles uniformly dispersed therein.

7. An apparatus according to claim 1, wherein the conductive polymleric material is a thermoplastic material with conductive particles uniformly dispersed therein.

8. An apparatus according to claim 1, wherein said passageway extending longitudinally through the conductive polymeric material comprises a tubular member disposed within the polymeric material.

9. An apparatus according to claim 8, wherein said tubular member is resiliently bendable.

10. An apparatus according to claim 1, wherin said one lumen is a first lumen and said tube has a second lumen, and said apparatus includes an inflatable balloon adjacent the distal end of the tube, said first lumen provides an air pathway to the balloon through the passageway extending longitudinally through the conductive polymeric material within said first lumen to provide for balloon inflation, and said second lumen is a through lumen extending at least substantially to the distal end and opens at a distal port.

11. An apparatus according to claim 1, wherein said one lumen is a first lumen and said tube has a second lumen and a third lumen and said apparatus includes an inflatable balloon adjacent the distal end of the tube, said second lumen extends to the balloon to provide for balloon inflation and said third lumen is a through lumen and extends at least substantially to the distal end and opens at a distal port.

12. An apparatus as defined in claim 1, wherein said electrode is a first electrode, said conductive lead is a first conductive lead, and said opening is a first opening, said tube has a second opening in the peripheral wall which extends from the lumen to the exterior of the tube, said second opening sized to expose a selected surface area of a second electrode to be formed therein, said second electrode comprising a conductive polymeric material filling said second opening and extending into said lumen proximally and distally of said second opening and extending radially outwardly no farther that the outer peripheral surface, and at least a second conductive lead having a distal end embedded within said conductive polymeric material at said second opening, and extending from the second electrode within the tube to the proximal end of the tube, said first conductive lead passing through said conductive polymeric material at said second opening.

13. A catheter for making electrical contact within the heart of a patient, comprising:
(a) an elongated tube sized to pass through a vein or an artery into the heart, said tube having proximal and distal ends, a peripheral wall having an outer surface, at least one lumen extending longitudinally within the tube, and an opening in the peripheral wall which extends from the lumen to the exterior of the tube, said opening sized to expose a selected surface area of an electrode to be formed therein;
(b) the electrode comprising a conductive polymeric material filling said opening and extending into said lumen proximally and distally of said opening, aid polymeric material having adhesive properties thereby creating an adhesive bond between the electrode and the tube, said electrode extending radially at said opening no farther that the outer surface of the peripheral wall;
(c) at least one conductive lead having a distal end encased within said conductive material and extending from said electrode within the tube to the proximal end of the tube; and
(d) a passageway extending longitudinally through the conductive polymeric material within said lumen.

14. A method of mounting electrodes within a lumen of a catheter, said catheter being sized to be received at a selected location within the body, said catheter having proximal and distal ends, a peripheral wall having an outer peripheral surface, and at least one lumen extending longitudinally within the catheter, comprising the steps of:
(a) cutting an opening in the peripheral wall of the catheter at a selected site along the length of the catheter, the opening sized to expose a selected surface area of an electrode to be formed therein;
(b) threading a conductive lead having a proximal end and a distal end through the lumen of the catheter to the selected site of the electrode so that the distal end of the conductive lead is positioned in the lumen at the opening in the peripheral wall;
(c) disposing in said lumen means for forming a passageway extending longitudinally through the electrode to be formed in said lumen at said opening; and
(d) introducing a conductive polymeric material in a semiliquid form into the opening so that it fills the opening, extends into the lumen a short distance proximally and distally of the opening, extends radially outward no farther than the outer peripheral surface and encircles the distal end of the conductive lead disposed within the lumen at the location of the opening and makes electrical contact with the distal end of the conductive lead, and so that said means for forming a passageway extends longitudinally through the conductive polymeric material.

* * * * *